US010258241B2

(12) United States Patent
Zalev et al.

(10) Patent No.: US 10,258,241 B2
(45) Date of Patent: Apr. 16, 2019

(54) PROBE ADAPTED TO CONTROL BLOOD FLOW THROUGH VESSELS DURING IMAGING AND METHOD OF USE OF SAME

(71) Applicant: Seno Medical Instruments, Inc., San Antonio, TX (US)

(72) Inventors: Jason Zalev, Thornhill (CA); Anthony Thomas Stavros, Denver, CO (US)

(73) Assignee: SENO MEDICAL INSTRUMENTS, INC., San Antonio, TX (US)

( * ) Notice: Subject to any disclaimer, the term of this patent is extended or adjusted under 35 U.S.C. 154(b) by 868 days.

(21) Appl. No.: 14/634,251

(22) Filed: Feb. 27, 2015

(65) Prior Publication Data

US 2015/0305628 A1    Oct. 29, 2015

Related U.S. Application Data

(60) Provisional application No. 61/945,557, filed on Feb. 27, 2014.

(51) Int. Cl.
*A61B 5/00* (2006.01)
*A61B 5/022* (2006.01)
(Continued)

(52) U.S. Cl.
CPC ............ *A61B 5/0095* (2013.01); *A61B 5/022* (2013.01); *A61B 5/026* (2013.01);
(Continued)

(58) Field of Classification Search
CPC ....... A61B 5/0095; A61B 5/022; A61B 5/026; A61B 5/14542; A61B 5/14551; A61B 5/14552; A61B 8/0825; A61B 8/0891
See application file for complete search history.

(56) References Cited

U.S. PATENT DOCUMENTS

| 4,267,732 A | 5/1981 | Quate |
| 5,504,281 A | 4/1996 | Whitney et al. |

(Continued)

FOREIGN PATENT DOCUMENTS

| EP | 0282234 A1 | 9/1988 | |
| JP | 2004089357 A * | 3/2004 | ............... A61B 8/00 |
| WO | 2013112626 A1 | 8/2013 | |

OTHER PUBLICATIONS

Ermilov, Sergey A., et al. "Laser optoacoustic imaging system for detection of breast cancer." Journal of biomedical optics 14.2 (2009): 024007-024007.

(Continued)

*Primary Examiner* — Bo Joseph Peng
(74) *Attorney, Agent, or Firm* — Dean D. Small; The Small Patent Law Group, LLC

(57) ABSTRACT

In an embodiment, an apparatus for opto-acoustic imaging includes a first contact area adapted to apply a first pressure to a surface of an imaging volume of a subject and a second contact area adapted to apply a second pressure to the surface. The second contact area is configured to provide decreased blood exit from the imaging volume by restricting flow relative to the first contact area. An optical energy output port is provided to illuminate the imaging volume to produce opto-acoustic signals from an absorbed optical energy of blood in the imaging volume. The opto-acoustic signals are detected by one or more ultrasound transducers and processed by a processor to generate images of the volume. An image generated by processing the detected opto-acoustic signals is output on a display.

20 Claims, 7 Drawing Sheets

(51) Int. Cl.
*A61B 5/026* (2006.01)
*A61B 5/145* (2006.01)
*A61B 5/1455* (2006.01)
*A61B 8/08* (2006.01)

(52) U.S. Cl.
CPC ...... *A61B 5/14542* (2013.01); *A61B 5/14551* (2013.01); *A61B 5/14552* (2013.01); *A61B 8/0825* (2013.01); *A61B 8/0891* (2013.01)

(56) References Cited

U.S. PATENT DOCUMENTS

| | | |
|---|---|---|
| 5,713,356 A | 2/1998 | Kruger |
| 5,840,023 A | 11/1998 | Oraevsky et al. |
| 5,977,538 A | 11/1999 | Unger et al. |
| 6,263,094 B1 | 7/2001 | Rosich et al. |
| 6,751,490 B2 | 6/2004 | Esenaliev et al. |
| 7,972,272 B2 | 7/2011 | Munce et al. |
| 8,016,419 B2 | 9/2011 | Zhang et al. |
| 8,025,406 B2 | 9/2011 | Zhang et al. |
| 8,144,327 B2 | 3/2012 | Nakajima et al. |
| 8,214,010 B2 | 7/2012 | Courtney et al. |
| 8,298,144 B2 | 10/2012 | Burcher |
| 8,300,224 B2 | 10/2012 | Nakajima et al. |
| 8,353,830 B2 | 1/2013 | Kanayama et al. |
| 8,353,833 B2 | 1/2013 | Dogra et al. |
| 8,460,195 B2 | 6/2013 | Courtney et al. |
| 8,480,584 B2 | 7/2013 | Kanayama et al. |
| 8,712,506 B2 | 4/2014 | Courtney et al. |
| 8,784,321 B2 | 7/2014 | Courtney et al. |
| 8,870,770 B2 | 10/2014 | Dogra et al. |
| 8,876,717 B2 | 11/2014 | Tokita et al. |
| 9,357,923 B2 | 6/2016 | Courtney et al. |
| 9,375,147 B2 | 6/2016 | Courtney et al. |
| 9,700,214 B2 | 7/2017 | Ichihara et al. |
| 2001/0022657 A1 | 9/2001 | Autrey et al. |
| 2005/0004458 A1 | 1/2005 | Kanayama et al. |
| 2006/0272418 A1* | 12/2006 | Maris ................ A61B 5/0097 73/606 |
| 2007/0167800 A1* | 7/2007 | Casula ................ G10K 11/346 600/459 |
| 2008/0071172 A1 | 3/2008 | Bruck et al. |
| 2009/0177083 A1 | 7/2009 | Matsumura |
| 2009/0221917 A1* | 9/2009 | Southern ............ A61B 5/0048 600/444 |
| 2010/0049044 A1 | 2/2010 | Burcher |
| 2010/0094134 A1 | 4/2010 | Zhu et al. |
| 2010/0179429 A1 | 7/2010 | Ho et al. |
| 2010/0249562 A1 | 9/2010 | Zhang et al. |
| 2010/0249570 A1 | 9/2010 | Carson et al. |
| 2010/0298688 A1 | 11/2010 | Dogra et al. |
| 2011/0054292 A1 | 3/2011 | Hirson et al. |
| 2011/0087107 A1 | 4/2011 | Lindekugel et al. |
| 2011/0166453 A1 | 7/2011 | Anthony et al. |
| 2011/0201914 A1 | 8/2011 | Wang et al. |
| 2011/0303015 A1 | 12/2011 | Ichihara et al. |
| 2011/0306857 A1 | 12/2011 | Razansky et al. |
| 2011/0319743 A1 | 12/2011 | Satoh |
| 2012/0083692 A1 | 4/2012 | Stoll |
| 2012/0165677 A1 | 6/2012 | Li et al. |
| 2013/0109950 A1* | 5/2013 | Herzog ................ A61B 8/0825 600/407 |
| 2013/0116538 A1* | 5/2013 | Herzog ................ A61B 5/743 600/407 |
| 2013/0190591 A1 | 7/2013 | Hirson et al. |
| 2013/0190595 A1 | 7/2013 | Oraevsky et al. |
| 2013/0279920 A1* | 10/2013 | Herzog .................... G02B 6/36 398/212 |
| 2013/0281819 A1* | 10/2013 | Schmid ................ A61B 5/0095 600/407 |
| 2013/0335441 A1 | 12/2013 | Zalev et al. |
| 2014/0007690 A1 | 1/2014 | Hirota |
| 2014/0051969 A1 | 2/2014 | Suzuki |
| 2014/0187902 A1 | 7/2014 | Sato et al. |
| 2014/0198606 A1 | 7/2014 | Morscher et al. |
| 2014/0221810 A1 | 8/2014 | Kacprowicz |
| 2014/0303476 A1 | 10/2014 | Dogra et al. |
| 2014/0323860 A1 | 10/2014 | Courtney et al. |
| 2015/0101411 A1 | 4/2015 | Zalev et al. |
| 2016/0249812 A1 | 9/2016 | Wang et al. |
| 2016/0302763 A1 | 10/2016 | Courtney et al. |
| 2017/0112474 A1 | 4/2017 | Burcher |

OTHER PUBLICATIONS

Hamilton, James D., et al. "High frequency optoacoustic arrays using etalon detection." IEEE transactions on ultrasonics, ferroelectrics, and frequency control 47.1 (2000): 160-169.

* cited by examiner

PROBE ADAPTED TO CONTROL BLOOD FLOW THROUGH VESSELS DURING IMAGING AND METHOD OF USE OF SAME

This application is a non-provisional of and claims priority to U.S. Provisional Patent Application No. 61/945,557 filed Feb. 27, 2014. The entire disclosure of that application, including the appendix thereto, is incorporated herein by reference. This application includes material which is subject to copyright protection. The copyright owner has no objection to the facsimile reproduction by anyone of the patent disclosure, as it appears in the Patent and Trademark Office files or records, but otherwise reserves all copyright rights whatsoever. This application relates to probes for use in connection with opto-acoustic imaging systems such as those described in U.S. patent application Ser. No. 14/512,896 filed Oct. 13, 2014, the entire disclosure of which is incorporated herein by reference.

FIELD

The present invention relates in general to the field of medical imaging, and in particular to an optoacoustic probe adapted to control blood flow through vessels during imaging.

BRIEF DESCRIPTION OF THE DRAWINGS

Objects, features, and advantages of the invention will be apparent from the following description of preferred embodiments as illustrated in the accompanying drawings, in which reference characters refer to the same parts throughout the various views. The drawings are not necessarily to scale, emphasis instead being placed upon illustrating principles of the invention. While the invention is amenable to various modifications and alternative forms, specifics thereof are shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

Figure 1A:
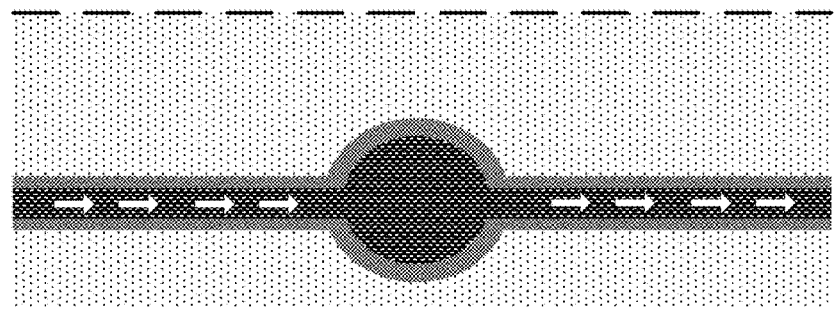
FIG. 1A shows a cross-sectional diagram of soft tissue with no object pressing against the tissue.

The following description and drawings are illustrative and are not to be construed as limiting. Numerous specific details are described to provide a thorough understanding. However, in certain instances, well-known or conventional details are not described in order to avoid obscuring the description. References to one or an embodiment in the present disclosure are not necessarily references to the same embodiment; and, such references mean at least one.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The systems and methods are described below with reference to, among other things, block diagrams, operational illustrations and algorithms of methods and devices to process optoacoustic imaging data. It is understood that each block of the block diagrams, operational illustrations and algorithms and combinations of blocks in the block diagrams, operational illustrations and algorithms, can be implemented by means of analog or digital hardware and computer program instructions.

These computer program instructions can be provided to a processor of a general purpose computer, special purpose computer, ASIC, or other programmable data processing apparatus, such that the instructions, which execute via the processor of the computer or other programmable data processing apparatus, implements the functions/acts specified in the block diagrams, operational block or blocks and or algorithms.

In some alternate implementations, the functions/acts noted in the blocks can occur out of the order noted in the operational illustrations. For example, two blocks shown in succession can in fact be executed substantially concurrently or the blocks can sometimes be executed in the reverse order, depending upon the functionality/acts involved.

Reference will now be made in more detail to various embodiments of the present invention, examples of which are illustrated in the accompanying drawings and the Appendix. As will be apparent to one of skill in the art, the calculations described in the Appendix and processing steps described in the Appendix may be implemented in a variety of other ways without departing from the spirit of the disclosure and scope of the invention herein. The Appendix is intended to show one manner of implementing the concepts disclosed herein the purpose of illustration and to facilitate understanding.

When an operator applies pressure to a probe that images tissue, blood may be flowed out of vessels or blood flow to vessels can be reduced. This problem may occur in Doppler ultrasound and other applications. In certain circumstances, to acquire clear images of vessels in Doppler ultrasound, an operator applies minimal pressure to avoid reducing blood flow, so the visibility of vessels is not reduced. In opto-acoustics, applying high pressure can also cause blood to flow out of vessels. However, in general applications of opto-acoustics, blood does not have to be flowing to be detected.

The methods and devices described herein provide illustrative examples of the subject invention including a probe for opto-acoustic imaging adapted to apply different pressure to different regions on the surface of tissue. In an embodiment, the methods and devices described herein control blood flow to a region being imaged. In an embodiment, the methods and devices described herein are applied to probes used for other types of testing. In an embodiment, the methods and devices described herein are applied to probes used for other medical or non-medical procedures involving tissue. In an embodiment, the methods and devices described herein are fitted or otherwise applied to instruments besides handheld probes, including scopes, instruments, equipment, and other apparatus used for imaging, testing, and other medical and non-medical procedures involving tissue.

In an embodiment, the methods and devices described herein are used for opto-acoustic imaging including, for example, breast imaging of tumors. It has been observed that applying high pressure with a probe can cause blood to flow out of vessels, which in some instances may reduce the quality of imaging tumors. In an embodiment, a probe adapted for opto-acoustic imaging, can be fitted to apply pressure to a region surrounding or adjacent to the imaging region, with a pressure different from the pressure applied over the imaging region, thereby controlling blood flow to the imaging region. In an embodiment, the imaging region comprises an acoustic receiver.

Figure 1B:
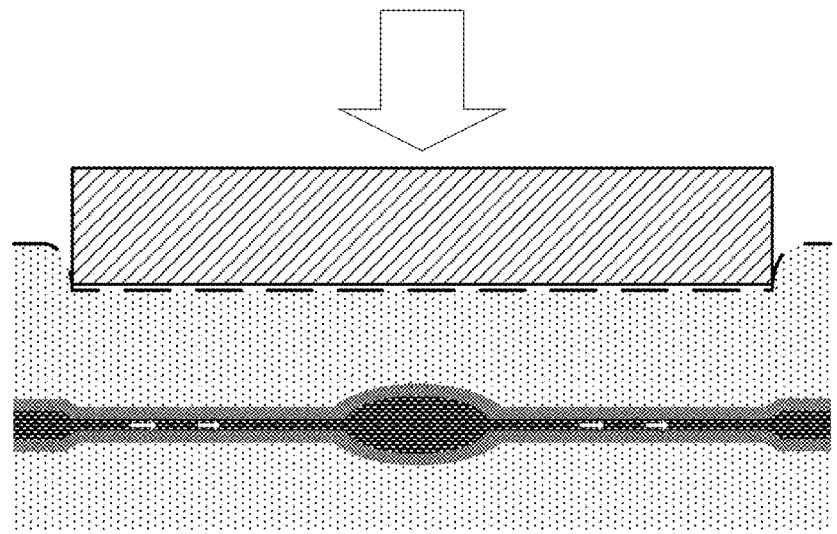
FIG. 1B shows a cross-sectional diagram of soft tissue with a flat object compressing the soft tissue.
Figure 1C:
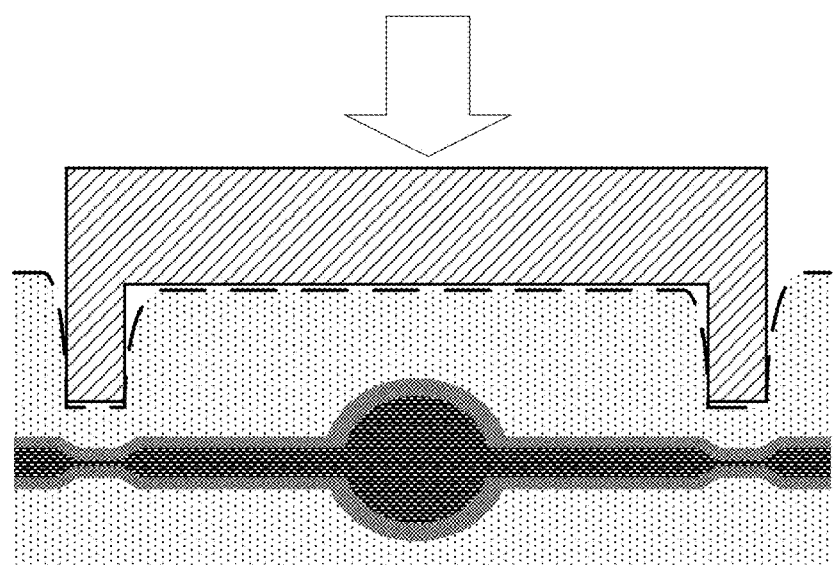
FIG. 1C shows a cross-sectional diagram of soft tissue with an object having a protrusion causing increased pressure to be applied to the exterior region, thereby trapping blood in the interior region.

The concept is illustrated in FIG. 1. Cross-sectional diagrams of soft tissue (e.g., breast tissue) are shown in FIGS. 1A, 1B and 1C. A feeding blood vessel is shown providing blood to a tumor, along with a draining vessel where blood can flow out of the tumor. In FIG. 1A, no object is pressing against the tissue. The tumor receives the full amount of blood and blood flows fully in the feeding and draining vessels. In FIG. 1B, a flat object is shown compressing the soft tissue. In the embodiment shown, the tumor and vessels are compressed, and less blood flows and less blood is contained in the tumor. In FIG. 1C, an object with a protrusion (e.g., a probe with a cup shaped appendage) is shown. The protrusion can cause increased pressure to be applied to the exterior region, thereby trapping blood in the interior region. The vessels directly under the protrusion are shown to be compressed, which restricts flow. Thus, in opto-acoustics, a probe (or other imaging setup) with the geometry described in FIG. 1c can create a beneficial situation for imaging when the blood is trapped in the lesion.

In embodiments, various amounts of pressure are applied to different regions of a surface of tissue, and the depth of deformation (a.k.a., strain, indentation) that occurs beneath a particular region. A mechanical model of the situation yields information for design of such an apparatus. More complex models are possible.

Figure 2:
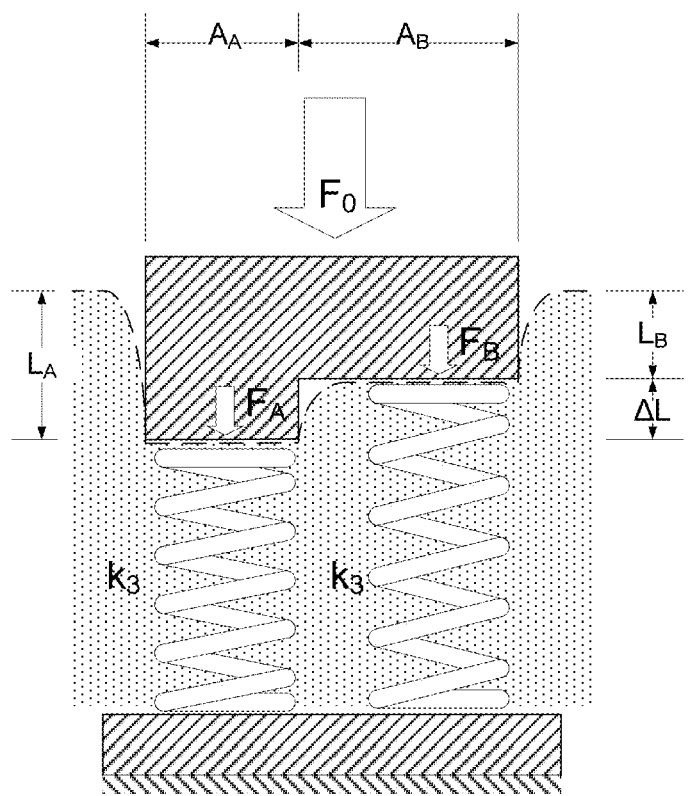
FIG. 2 shows a cross sectional diagram illustrating a model approximating tissue to obey linear elastic relations.

In FIG. 2, a model approximating tissue to obey linear elastic relations is shown in cross-section. The diagram in FIG. 2 is a simplified model to show linear elastic relations of tissue indentation for using a rigid member. The linear elastic relations represented here can be applied to the embodiment of FIG. 1C even though FIG. 1C may look different than FIG. 2; the proper equations for the different looking shape are encompassed by the simplified model as shown, as would be apparent to one skilled in the art. In the model, the tissue compressibility is shown diagrammatically as a spring with a spring constant, the value of which is $k_3$. The operator applies a force F0 to the object as shown. The object has two faces, A and B, that contact the tissue. The surface area of the faces are $A_A$ and $A_B$ respectively. The face areas are not necessarily rectangular, but indicate the total surface area for a face of type A and for a face of type B. The faces of each type can, in different embodiments, be formed into many different shapes that are equivalent to the model. Face A protrudes further than face B by a distance of $\Delta L$, as shown. If it is desired that face B protrudes greater than face A, then $\Delta L$ can be assigned a negative value. The depth of tissue indentation for the faces are $L_A$ and $L_B$. The schematic shown in FIG. 2 is also applicable to the situation of FIG. 1C, where a cup surrounds an inner region (In this case, they are the same if FIG. 2 is revolved about an axis). In an embodiment, sufficient force is applied so that both faces are in contact with the tissue. As shown in the calculations in the appendix, $$L_A = F0/((A_A+A_B)*k_3) + A_B*\Delta L/(A_A+A_B),$$

and $$L_B = F0/((A_A+A_B)*k_3) - A_A*\Delta L/(A_A+A_B) = L_A - \Delta L.$$

The pressure underneath each face is given by $$P_A = k_3 * L_A,$$

and $$P_B = k_3 * L_B.$$

In the equations and models shown herein, the relations between pressure and force (PRESSURE=FORCE/AREA) are assumed to be handled appropriately, and when solving equations, one skilled in the art will know in which circumstances an equation requires the use of pressure units rather than force units. Force is the integral of pressure with respect to area.

Of further interest is the situation where the probe comprises soft materials that may be compressed. The compressibility of the probe material also determines the depths of deformation, and the pressure applied to each region. Furthermore, in an embodiment, for a given amount of operator force, the compressibility of the probe material can allow greater control of the pressure applied to each region, in particular, to control the pressure in the imaging region.

Figure 3:
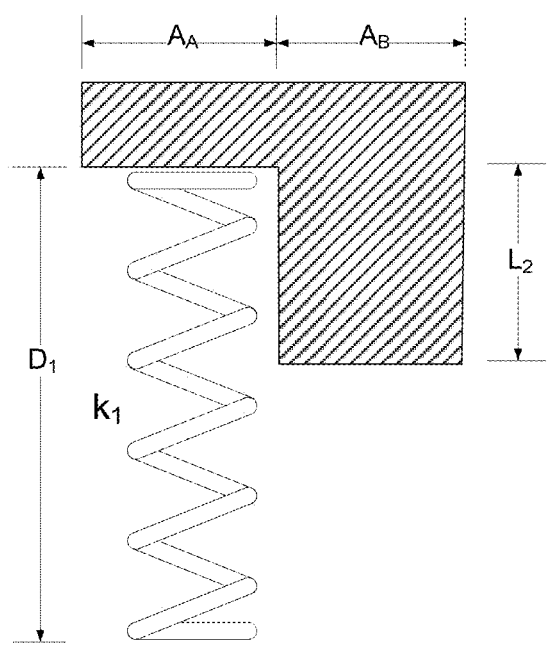
FIG. 3 shows a schematic diagram modeling indentation by a rigid member in accordance with an embodiment.
Figure 4:
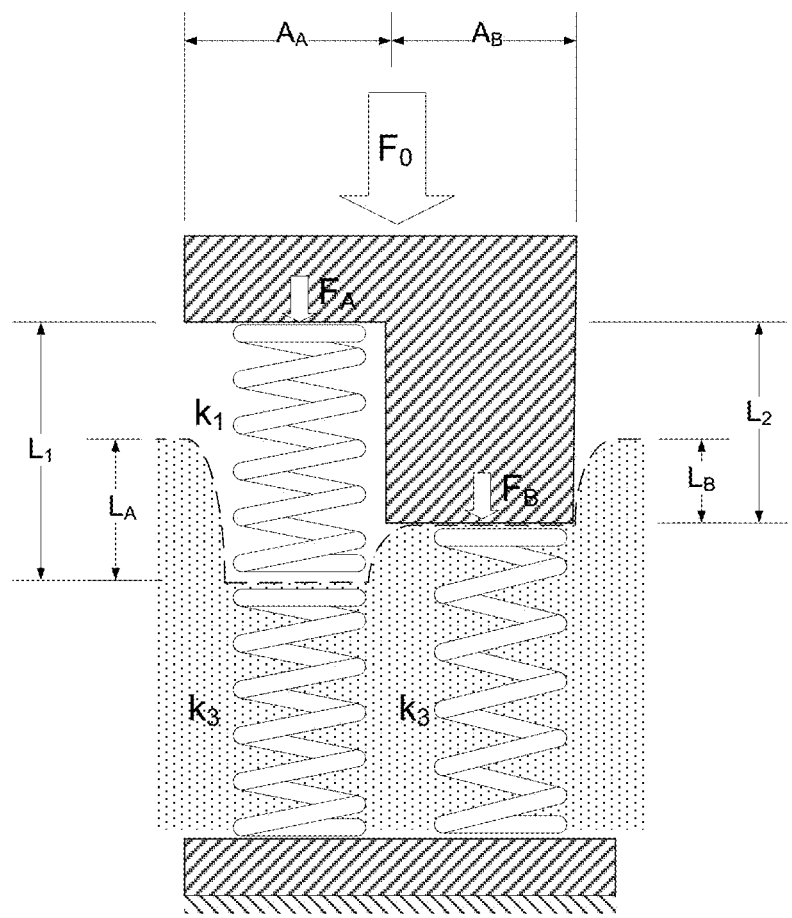
FIG. 4 shows a schematic diagram modeling indentation by a compressible member in accordance with an embodiment.

FIG. 3 shows a schematic with a compressible member. The length $D_1$ is the uncompressed length of the compressible member. $L_2$ is the protruding length of an incompressible member (representing, e.g., an imaging region). The schematic is applicable to a compressible cup (e.g. made of rubber, foam or soft material, etc.) around a probe if FIG. 3 is revolved about an axis. FIG. 4 shows this probe applied to tissue in cross-section. In FIG. 4, the compressible member is compressed, so the length is called $L_1$, which is the compressed length, not the uncompressed length, $D_1$. As before, the depth of tissue indentation for the faces are $L_A$ and $L_B$, and the surface area of the faces are $A_A$ and $A_B$. It is shown in the calculations in the appendix that:

$$L_A = (k_1/k_3 * F0 + A_B*(D_1-L_2)*k_1)/(k_1*A_A+(k_1+k_3)*A_B),$$

and $$LB = ((k1+k3)/k3*F0 - AA*(D1-L2)*k1)/(k1*AA+(k1+k3)*AB).$$

Thus, in an embodiment, the surface pressure and tissue indentation can be controlled by designing a probe with appropriate parameters $A_A$, $A_B$, $k_1$, $D_1$ and $L_2$. In an embodiment, the depth of indentation (and the pressure) of a face increases when the surface area of that face decreases. This is the "knife" effect, where if the same force were applied to a very small surface area, a high pressure and indentation would result over a small surface area. Furthermore, in an embodiment, when k1 is increased, this causes the indentation of face A to increase, and of face B to potentially decrease. Thus, in an embodiment, when a compressible material is used to apply pressure to the exterior region, the protruding length D1 of this compressive member may be longer than if it were an incompressible member (i.e., where D1=L1 and k1 is large) to have the same effect.

Figure 5:
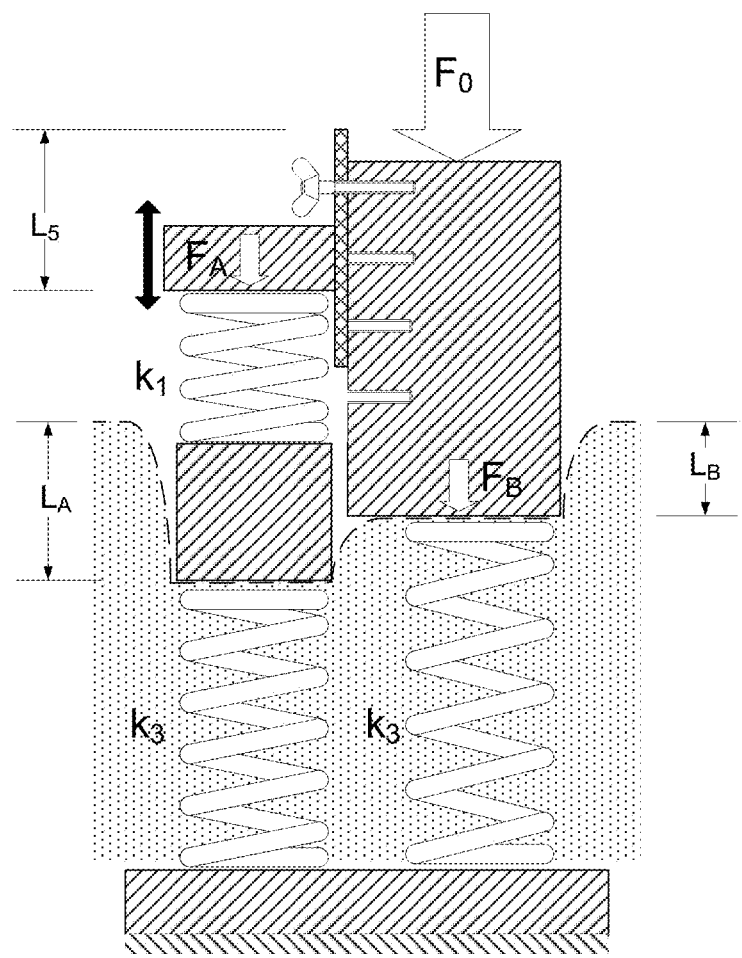
FIG. 5 shows a schematic diagram modeling indentation by a compressible member in accordance with an embodiment.

In an embodiment shown in FIG. 5, adjustable compressibility parameters are used. In an embodiment, the probe has a mechanism to adjust the protruding length. In an embodiment, the adjustment is electronically controlled. The adjustment may occur inside of the probe, and is not limited to what is shown in the schematic. The schematic of FIG. 5 shows a manually adjustable protruding length of the probe. In a similar manner it may also be possible to manually or electronically control the compressibility, not only just the protruding length. FIG. 5 also illustrates that an incompressible member may be placed on the distal surface of a probe that is attached to the compressible member. In an embodiment, this may correspond to an illumination member (e.g. light bar, light path, optical window, diffuser), or an alternate embodiment, an acoustic receiver. The member may also be optically reflective, optically transparent, or acoustically absorbing.

A method for diagnosis using different settings of compression is now described. The metabolism of tissue (and tumors) consume oxygen from the blood supply. When the blood flow is constricted, the oxygenation level of the tumor (and tissue) may be reduced. In such circumstances, different types of tissues or structures may exhibit different metabolic behavior for the constricted or non-constricted cases. For example, when constricted, a malignancy might become very much more strongly deoxygenated than a benign mass in the same circumstances. Furthermore, the rates at which the oxygenation levels of the lesion become deoxygenated may be dependent upon the metabolic factors of the tissue. These rates may also be examined.

Accordingly, a method is described wherein a volume of tissue is imaged with an opto-acoustic imaging apparatus, comprising: configuring the apparatus to collect data for imagery of tissue using at least one optical illumination wavelength for a first configuration of applied surface pressure; reconfiguring the apparatus to collect data for imagery of tissue using at least one optical illumination wavelength for a second configuration of applied surface pressure, where the second configuration of applied surface pressure is configured to trap blood or reduce flow in the imaging region moreso than in the first configuration; analyzing the first data for imagery and second data for imagery to determine the difference in at least one parameter; and creating an image of the at least one parameter as spatially represented in the volume. In an embodiment, the at least one parameter is selected from: blood oxygen saturation, blood volume, optical fluence, or other property. In an embodiment, data from a continuum of applied surface pressure configurations is acquired by applying incremental changes to the surface pressure configuration and collecting data for imagery at each increment. In an embodiment, this is done by increasing a length (e.g. L5 as shown in FIG. 5). As an example, in an embodiment, the first configuration could use a length L5 of 0 cm, and the second configuration could use a length L5 of 1 cm. As described herein, other configurations are possible. In an embodiment, it can be electronically controlled. In an embodiment, the first and second data for imagery are analyzed by subtractive analysis. In an embodiment, for an amount of time following the event of applying (or releasing) of the blood trapping pressure configuration, multiple frames of data are collected, where each frame corresponds to a time since the event, and creating output corresponding to the time domain behavior of metabolic or blood flow activity that is produced from the multiple frames. In an embodiment, an image that represents change per unit time of the at least parameter, as spatially represented in the tissue is presented. In an embodiment, the rate of de-oxygenation (e.g. of the tumor of tissue) is presented. In an embodiment the rate of blood returning flow is presented.

Force (or pressure), or distance sensors may be positioned on faces of the probe or other instrument. In an embodiment, there is a desired pressure (or distance) that is optimal for imaging. For example, low non-zero pressure to the imaging region, and high pressure to the constrictive region. An indicator on the screen can be presented to the operator to indicate applying more, less, or sufficient pressure. In an embodiment, the pressure sensor can be used to control the adjustable compressibility automatically. For example, if a desired constrictive pressure is not met, the constrictive pressure can be increased. Also, for example, if contact is not made with the acoustic receiver, adjustment can be made to allow contact without varying the operator force.

In an embodiment, the compressibility of the tissue, k3, can be measured. This can be done by solving the above equations. This may involve sensors for (directly or indirectly) measuring LA and/or LB and/or F0.

Figure 6:
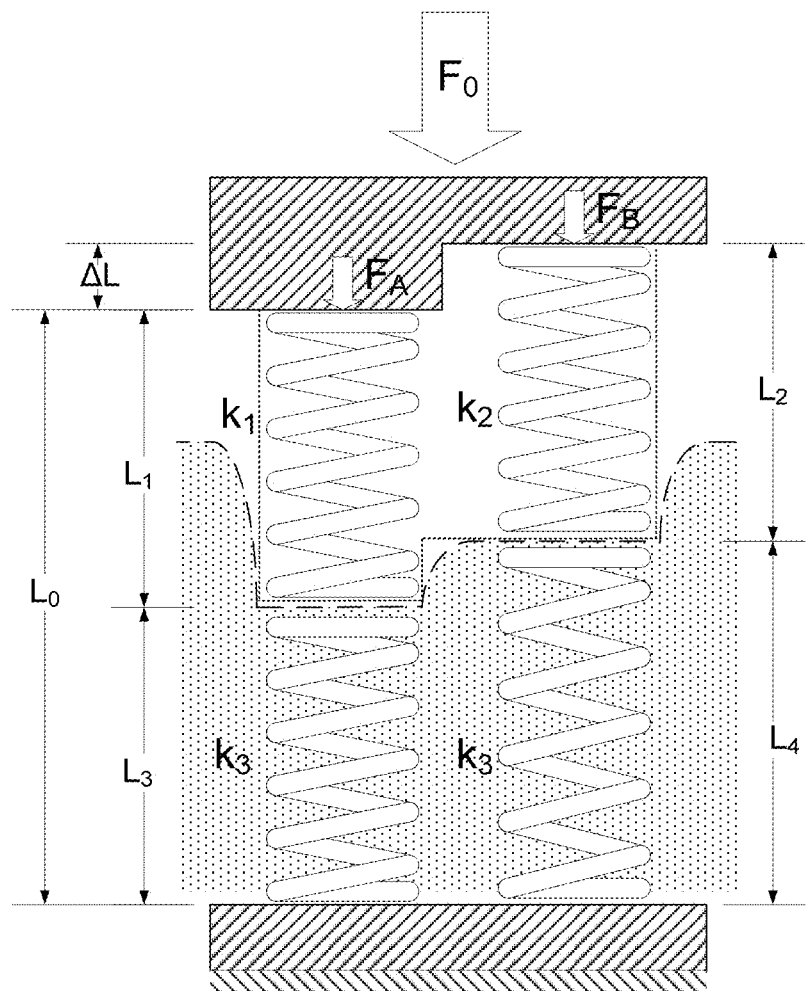
FIG. 6 shows a schematic diagram modeling indentation by multiple compressible members in accordance with an embodiment.

In FIG. 6, multiple compressive members are shown in cross-section to illustrate a scenario where multiple compressive members are present, which can be solved similar to equations described in the appendix.

Figure 7:
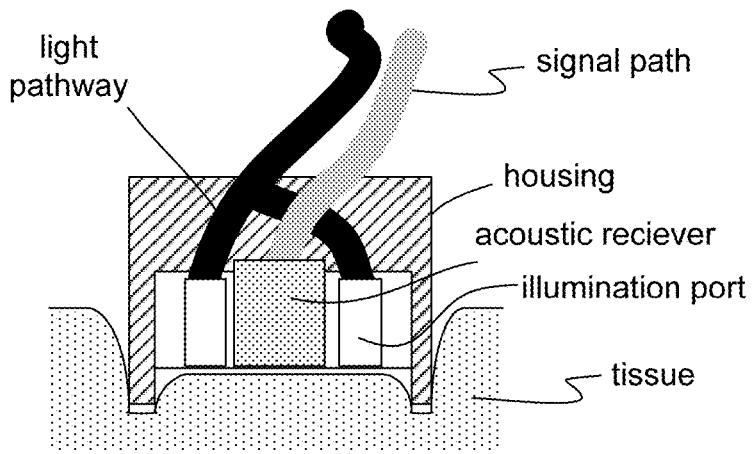
FIG. 7 shows a cross sectional diagram illustrating an opto-acoustic probe in accordance with an embodiment.

In FIG. 7, a cross-section of an embodiment of an opto-acoustic probe is shown. Different light delivery and acoustic receiver configurations are possible.

Figure 8:
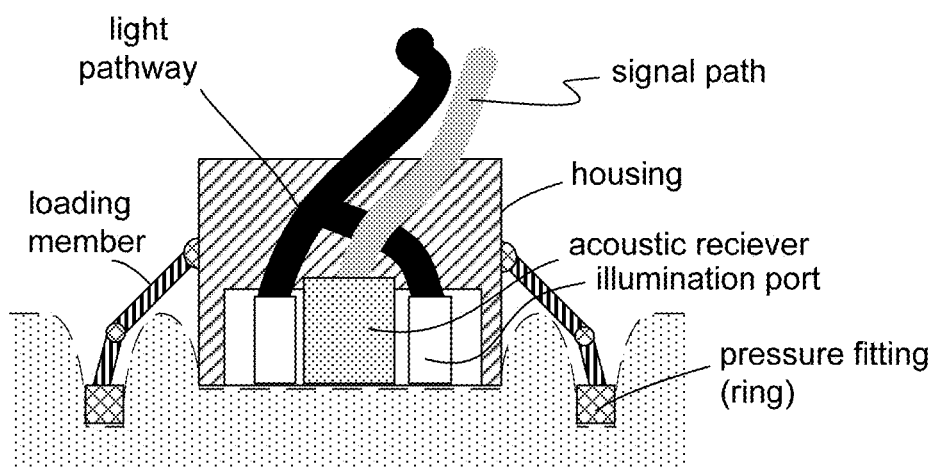
FIG. 8 shows a cross sectional diagram illustrating an opto-acoustic probe in accordance with an embodiment in which a pressure fitting is fitted around the probe to apply pressure to the tissue.

In FIG. 8, a cross-section of an embodiment of an opto-acoustic probe is shown. A pressure fitting, such as a ring or a cup, can be fitted around the probe to apply pressure to the tissue. The loading member can attach the fitting to the probe. In an embodiment, the loading member may permit the ring to be engaged or disengaged, or have the amount of pressure be varied, or adjusted.

In an embodiment, the probe can automatically apply a desired pressure (and/or a desired indentation) to one or both of the contact areas of the probe. In an embodiment, this can be done dynamically based on an amount of force applied by an operator. In an embodiment, a control unit can adjust the amount of force, pressure and/or distance that is distributed to one or more contact regions by an applied force. In an embodiment, the pressure applied to one of the regions of tissue can be controlled by an opto-acoustic probe.

In an embodiment, the dynamic probe comprises ultrasonic transducers to receive acoustic signals produced in response to absorption of optical energy, a first contact area to apply a first force to a first region of tissue, a second contact area to apply a second force to a second region of tissue, one or more sensors to measure at least one of the first force and the second force, and an adjustable member with a setting to adjust or set the first force. In an embodiment, the adjustable member is controlled electronically. In an embodiment, the pressure can be controlled by performing the following steps: a.) setting the adjustable member to an initial configuration; b.) recording a measurement from the one or more sensors (after the probe has been placed into contact with the tissue); c.) changing the setting of the adjustable member based upon the measurement from the one or more sensors; and, d.) repeating steps b.) and c.) until a desired pressure applied to the first region of tissue is reached. The volume can then be illuminated with electromagnetic energy to produce opto-acoustic acoustic signals using optimal application of forces.

In an embodiment, dynamic adjustment is applied to a handheld probe. A total applied force is applied to the probe by an operator, wherein a portion of the total applied force is distributed to the first force that is applied to the first region of tissue. In an embodiment, the probe comprises a sensor for measuring the total applied force, in addition to a sensor for measuring one other force. In an embodiment, a force sensor can be implemented by measuring distance and converting to force. In an embodiment, the desired pressure setting applied to a region equals a fixed proportion of the total applied force. In an embodiment, 80% of the applied force is applied to the pressure fitting. In an embodiment, between 80% and 100% of applied pressure is applied to the pressure fitting. In an embodiment, a configuration setting of between 10% and 90% of the applied force and/or applied pressure is applied to the pressure fitting. In an embodiment, a configuration setting of 0% of the applied force is applied to the pressure fitting, the pressure fitting being disengaged. In an embodiment, a configuration setting of 100% of the applied force is applied to the pressure fitting, the transducer being disengaged or lightly contacting but remaining coupled to the volume. In an embodiment, the force applied to the pressure fitting is set to apply a minimal force to the transducer while the transducer remains coupled. In an embodiment, when substantially zero force is applied to the transducer (and substantially 100% force is applied to the pressure fitting), and the transducer remains coupled, other physical principles (e.g. attractive forces) may serve to keep the transducer coupled. In an embodiment, applying low force to the imaging region prevents squeezing of blood out of vessels for imaging even while flow is reduced to the vessels by the pressure fitting. In an embodiment, the total applied force is equal to the sum of force for the first region plus force for the second region. In an embodiment, the sensor for measuring the total applied force computes a sum of a measurement from a sensor for measuring force for the first region and a measurement from a sensor for measuring the force for the second region. In an embodiment, a force sensor, a pressure sensor, and/or a distance sensor may be used to compute a force.

In an embodiment, changing the setting of the adjustable member can be done by: determining a value of pressure applied to the first region of tissue by processing the measurements of one or more sensors; computing a difference between a desired pressure for first region of tissue and the determined immediate value for pressure for the first region of tissue; determining an amount for the setting change based upon the computed difference; and changing the setting of the adjustable member by the determined amount.

In an embodiment where the ultrasonic transducers are located on the second contact area, the second region of tissue comprises an imaging volume comprising blood. The desired pressure applied to the first region of tissue can decrease blood exit from the imaging volume by restricting flow. It should be apparent that the flow can be restricted moreso than if the contact region for the imaging volume were used in isolation (e.g. without a pressure fitting), as blood would be pushed out by force applied to the contact area for the imaging region and/or any constriction by the pressure fitting would not occur. This can improve quality in an image representing absorbed optical energy of blood within the imaging volume.

In an embodiment, an image spatially representing the difference between two configurations is produced and displayed. In an embodiment, this is done by imaging one configuration as described above and the performing the following steps to achieve another configuration: repeating the above steps b.) and c.) until a second desired pressure applied to the first region of tissue is reached; illuminating the volume with optical energy in this configuration to produce additional acoustic signals that are received by the ultrasonic transducers; and processing the acoustic signals from both configurations to determine a difference of absorbed optical energy for the first desired pressure and the second desired pressure; and, outputting to a display an image spatially representing the difference. In an embodiment, the image is of a lesion in breast tissue.

The present devices and methods are described above with reference to block diagrams and operational illustrations. It is understood that each block of the block diagrams or operational illustrations, and combinations of blocks in the block diagrams or operational illustrations, may be implemented by means of analog or digital hardware and computer program instructions. These computer program instructions may be provided to a processor of a general purpose computer, special purpose computer, ASIC, FPGA or other programmable data processing apparatus, such that the instructions, which execute via the processor of the computer or other programmable data processing apparatus, implements the functions/acts specified in the block diagrams or operational block or blocks. In some alternate implementations, the functions/acts noted in the blocks may occur out of the order noted in the operational illustrations. For example, two blocks shown in succession may in fact be executed substantially concurrently or the blocks may sometimes be executed in the reverse order, depending upon the functionality/acts involved.

As used in this description, "a" or "an" means "at least one" or "one or more" unless otherwise indicated. In addition, the singular forms "a", "an", and "the" include plural referents unless the content clearly dictates otherwise. Thus, for example, reference to a composition containing "a compound" includes a mixture of two or more compounds.

As used in this specification, the term "or" is generally employed in its sense including "and/or" unless the content clearly dictates otherwise.

The recitation herein of numerical ranges by endpoints includes all numbers subsumed within that range (e.g. 1 to 5 includes 1, 1.5, 2, 2.75, 3, 3.80, 4, and 5).

Unless otherwise indicated, all numbers expressing quantities of ingredients, measurement of properties and so forth used in the specification and claims are to be understood as being modified in all instances by the term "about," unless the context clearly dictates otherwise. Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, each numerical parameter should at least be construed in light of the number of reported significant digits and by applying ordinary rounding techniques. Any numerical value, however, inherently contains certain errors necessarily resulting from the standard deviations found in their respective testing measurements.

Those skilled in the art will recognize that the methods and devices of the present disclosure may be implemented in many manners and as such are not to be limited by the foregoing exemplary embodiments and examples. In other words, functional elements being performed by single or multiple components, in various combinations of hardware and software or firmware, and individual functions, may be distributed among software applications at either the client level or server level or both. In this regard, any number of the features of the different embodiments described herein may be combined into single or multiple embodiments, and alternate embodiments having fewer than, or more than, all of the features described herein are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, as well as those variations and modifications that may be made to the hardware or software or firmware components described herein as would be understood by those skilled in the art now and hereafter.

Furthermore, the embodiments of methods presented and described as flowcharts in this disclosure are provided by way of example in order to provide a more complete understanding of the technology. The disclosed methods are not limited to the operations and logical flow presented herein. Alternative embodiments are contemplated in which the order of the various operations is altered and in which sub-operations described as being part of a larger operation are performed independently.

Various modifications and alterations to the invention will become apparent to those skilled in the art without departing from the scope and spirit of this invention. It should be understood that the invention is not intended to be unduly limited by the specific embodiments and examples set forth herein, and that such embodiments and examples are presented merely to illustrate the invention, with the scope of the invention intended to be limited only by the claims attached hereto. Thus, while the invention has been particularly shown and described with reference to a preferred embodiment thereof, it will be understood by those skilled in the art that various changes in form and details may be made therein without departing from the spirit and scope of the invention.

APPENDIX TO THE SPECIFICATION

Pressure/Force/Area Relations $$A0=AA+AB$$

$$A0=AA+AB \tag{1.1}$$

$$P=\frac{F}{A} \quad P=\frac{F}{A} \tag{1.2}$$

$$F0=FA+FB$$

$$F0=FA+FB \tag{1.3}$$

$$P0 \cdot A0 = PA \cdot AA + PB \cdot AB \tag{1.4}$$

$$P0 \cdot A0 = PA \cdot AA + PB \cdot AB \tag{1.5}$$

$$F0=P0 \cdot A0$$

$$F0=P0 \cdot A0 \tag{1.6}$$

$$FA=PA \cdot AA$$

$$FA=PA \cdot AA \tag{1.7}$$

$$FB=PB \cdot AB$$

$$FB=PB \cdot AB \tag{1.8}$$

Spring Energy

Let the compression of the spring be x1, and the compression of the tissue be LA=x3, then the total compression is x0. The energy is given by:

$$E=k1 \cdot x1^2 + k3 \cdot x3^2$$

$$E=k1 \cdot x1^2 + k3 \cdot x3^2 \tag{2.1}$$

With the total compression x0:

$$x1+x3=x0$$

$$x1+x3=x0 \tag{2.2}$$

substitute in for x3:

$$\text{eval}((2.1),x3=\text{solve}((2.2),x3)$$

$$E=k1x1^2+k3(x0-x1)^2 \tag{2.3}$$

Setting dE=0, and solving for x1, we get:

$$x1=\text{solve}(\text{diff}((2.3),x1),x1)$$

$$x1=\frac{k3 x0}{k1+k3} \tag{2.4}$$

Thus x3 is:

$$x3=\text{solve}(\text{eval}((2.2),(2.4)),x3)$$

$$x3=\frac{x0 k1}{k1+k3} \tag{2.5}$$

$$x3:=LA$$

$$LA \tag{2.6}$$

Thus the total compression in path A is:

$$x0=\text{solve}(\text{eval}((2.2),(2.4)),x0)$$

$$x0=\frac{LA(k1+k3)}{k1} \tag{2.7}$$

or the compressed spring length, in terms of tissue length is:

$$\text{eval}((2.4),(2.7))$$

$$x1 = \frac{k3\ LA}{k1} \quad (2.8)$$

Forces Applied to the Tissue

In the spring/tissue path, we have an effective spring constant k_eff:

$$k_{\text{eff}} = \left(\frac{1}{k1} + \frac{1}{k3}\right)^{-1} \quad k_{\text{eff}} = \frac{1}{\frac{1}{k1} + \frac{1}{k3}} \quad (3.1)$$

So the total pressure force in path A is:

$PA = k_{\text{eff}} \cdot x0$ $PA = k_{\text{eff}} x0$ (3.2)

Thus FA is:

$FA = \text{eval}(PA \cdot AA, (3.2))$ $FA = k_{\text{eff}} x0 AA$ (3.3)

Or expanded out:

simplify(eval((3.2),(3.1)))

$$PA = \frac{k1\ k3\ x0}{k1 + k3} \quad (3.4)$$

And the total pressure force in path B is:

$PB = k3 \cdot LB$ $PB = k3 LB$ (3.5)

And thus FB is:

$FB = \text{eval}(PB \cdot AB, (3.5))$ $PB = k3 LB\ AB$ (3.6)

So assuming both paths are in contact with the tissue, F0 is FA+FB:

$F0 = \text{eval}(FA + FB, \{(3.3), (3.6)\})$ $F0 = k_{\text{eff}} x0 AA + k3 LB\ AB$ (3.7)

which is to say:

collect(simplify(eval((3.7),(3.1))),[x0,LB],factor)

$$F0 = \frac{k3\ k1\ AA\ x0}{k1 + k3} + k3\ LB\ AB \quad (3.8)$$

And we can also simplify it to an expression that could be directly written as:

eval((3.8),(2.7))

$F0 = k3 AA\ LA + k3 LB\ AB$ (3.9)

Which is:

collect((3.9),k3,sort)

$F0 = (AA\ LA + AB\ LB)k3$ (3.10)

original length of spring 1:

$D1 = L1 + x1$ $D1 = L1 + x1$ (3.11)

difference between uncompressed spring length D1 and fixed baffle length L2 is:

$DL = (D1) - L2$ $DL = (D1) - L2$ (3.12)

So the compressed spring length L1 is:

$L1 = \text{solve}((3.11), L1)$ $L1 = -x1 + D1$ (3.13)

difference between compressed spring and fixed baffle length is the same as the difference in tissue compressions $L1 - L2 = LA - LB$ $L1 - L2 = LA - LB$ (3.14)

Thus:

eval((3.14),(3.13))

$-x1 + D1 - L2 = LA - LB$ (3.15)

And from above, we can find LB in terms of LA as:

$LB = \text{collect}((\text{solve}(\text{eval}((3.15),(2.8)),LB)),[LA],\text{simplify})$ $$LB = \frac{LA(k1 + k3)}{l1} - D1 + L2 \quad (3.16)$$

We can substitute this back into the expression for F0 eval((3.10),(3.16))

$$F0 = \left(AA\ LA + AB\left(\frac{LA(k1 + k3)}{k1} - D1 + L2\right)\right)k3 \quad (3.17)$$

And this yields the solution to the tissue compressed distances LA and LB in terms of the applied force F0, $LA = \text{collect}(\text{solve}((3.17),LA),F0,\text{factor})$ $$LA = \frac{k1\ F0}{(k1\ AA + AB\ k1 + k3\ AB)k3} + \frac{AB(D1 - L2)k1}{k1\ AA + AB\ k1 + k3\ AB} \quad (3.18)$$

$LB = \text{collect}(\text{solve}(\text{eval}((3.16),(3.18)),LB),F0,\text{factor})$ $$LB = \frac{(k1 + k3)F0}{(k1\ AA + AB\ k1 + k3\ AB)k3} - \frac{k1\ AA(D1 - L2)}{k1\ AA + AB\ k1 + k3\ AB} \quad (3.19)$$

The Pressure PB over the tissue in terms of the force thus:

collect(simplify(eval((3.5),(3.19))),F0,factor) (3.20)

$$PB = \frac{(k1 + k3)F0}{k1\ AA + AB\ k1 + k3\ AB} - \frac{k1\ AA(D1 - L2)k3}{k1\ AA + AB\ k1 + k3\ AB} \quad (3.21)$$

And the pressure PA over the tissue in terms of the force is:

collect(eval((3.4),eval((2.7),(3.18))),F0,factor)

$$PA = \frac{k1\ F0}{k1\ AA + AB\ k1 + k3\ AB} + \frac{k1\ AB(D1 - L2)k1}{k1\ AA + AB\ k1 + k3\ AB} \quad (3.22)$$

In the limit as the spring becomes infinitely stiff:

collect(limit((3.18),k1=infinity),F0,factor)

$$LA = \frac{F0}{(AA + AB)k3} + \frac{(D1 - L2)AB}{AA + AB} \quad (3.23)$$

collect(limit((3.19),k1=infinity),F0,factor)

$$LB = \frac{F0}{(AA + AB)k3} - \frac{AA(D1 - L2)}{AA + AB} \quad (3.24)$$

collect(limit((3.22),k1=infinity),F0,factor)

$$PA = \frac{F0}{AA + AB} + \frac{(D1 - L2)k3\ AB}{AA = AB} \quad (3.25)$$

collect(limit((3.21),k1=infinity),F0,factor)

$$PB = \frac{F0}{AA + AB} - \frac{AA(D1 - L2)k3}{AA + AB} \quad (3.26)$$

The invention claimed is:

1. An apparatus, comprising:
a probe having a face including a first contact area adapted to apply a first pressure to a surface of an imaging volume of a subject;
one or more ultrasound transducers provided at the face of the probe;
an optical energy output port configured to produce opto-acoustic signals from an absorbed optical energy of blood in the imaging volume, the opto-acoustic signals being detected by the one or more ultrasound transducers and processed by a processor to generate images of the volume;
wherein the probe includes a cup-shaped appendage, the cup-shaped appendage including a second contact area provided about the face of the probe, wherein the second contact area restricts flow of the blood relative to that of the first contact area; and
a display to output an image generated by processing the detected opto-acoustic signals.

2. The apparatus of claim 1, wherein the second contact area surrounds the first contact area.

3. The apparatus of claim 1, wherein the probe has a housing that includes the cup-shaped appendage.

4. The apparatus of claim 3, wherein the housing includes an edge that is located distal to the first contact area and includes the second contact area.

5. The apparatus of claim 4, wherein the edge surrounds the first contact area.

6. The apparatus of claim 3, wherein the housing include an edge that lies on a same plane as the first contact area.

7. The apparatus of claim 3, wherein the cup-shaped appendage includes a loading member coupled to the housing of the probe and extending about the face.

8. The apparatus of claim 7, wherein the loading member couples to the housing at a first end proximal to the first contact area and extends to a second end distal to the first contact area.

9. The apparatus of claim 7, wherein a pressure fitting is secured to the loading member and extends about the face.

10. The apparatus of claim 9, wherein the pressure fitting includes the second contact area of the probe.

11. The apparatus of claim 9, wherein the pressure fitting is a ring.

12. The apparatus of claim 7, wherein the loading member is configured to move to cause the second contact area to engage and disengage the imaging volume.

13. The apparatus of claim 12, wherein the loading member is further configured to move to cause the second contact area to engage the volume when the first contact area is not in contact with the volume.

14. The apparatus of claim 1, wherein the first contact area of the face is a linear surface.

15. The apparatus of claim 14, wherein the first contact area forms a first plane and the second contact area forms a second plane distal to the first plane.

16. An apparatus, comprising:
a probe including a housing having a face including a first contact area adapted to apply a pressure to a surface of an imaging volume of a subject;
one or more ultrasound transducers provided at the face of the probe;
an optical energy output port configured to produce opto-acoustic signals from an absorbed optical energy of blood in the imaging volume, the opto-acoustic signals being detected by the one or more ultrasound transducers and processed by a processor to generate images of the volume;
a loading member coupled to the housing and extending from the housing to distal the first contact area of the housing; the loading member including a pressure fitting having a second contact area of the probe configured to engage the surface of the imaging volume.

17. The apparatus of claim 16, wherein the loading member is movably coupled to housing to move relative to the housing.

18. The apparatus of claim 16, wherein the pressure fitting is a ring that surrounds the first contact area.

19. The apparatus of claim 16, wherein the face is an edge of the housing.

20. The apparatus of claim 19, wherein the face is a linear surface.

* * * * *